United States Patent [19]

Banchereau et al.

[11] Patent Number: 4,948,738

[45] Date of Patent: Aug. 14, 1990

[54] MONOCLONAL ANTIBODIES TO GAMMA-INTERFERON, HYBRIDOMAS PRODUCING SUCH ANTIBODIES, AND KIT FOR USING SUCH ANTIBODIES

[75] Inventors: Jacques Banchereau, Ecully; Odile Djossou, Lyon; John Wijdenes, Lyon; Hélène Cabrillat, Lyon; Catherine Favre, Lyon, all of France

[73] Assignee: Laboratoires UNICET, Levallois-Perret, France

[21] Appl. No.: 380,760

[22] Filed: Jul. 14, 1989

Related U.S. Application Data

[63] Continuation of Ser. No. 26,722, filed as PCT EP86/00389 on Jul. 2, 1986 published as WO87/00182 on Jan. 15, 1987, abandoned.

[30] Foreign Application Priority Data

Jul. 5, 1985 [FR] France ................................ 8510346

[51] Int. Cl.$^5$ ........................................... G01N 33/577
[52] U.S. Cl. ......................................... 456/531; 435/7; 435/70.21; 435/172.2; 435/240.27; 436/548; 436/815; 935/104; 935/108
[58] Field of Search ............. 435/7, 68, 172.2, 240.27; 436/548, 531; 935/104, 108

[56] References Cited

U.S. PATENT DOCUMENTS

| | | |
|---|---|---|
| 4,499,014 | 2/1985 | Estis . |
| 4,599,306 | 7/1986 | Altrock .................. 935/110 X |
| 4,666,865 | 5/1987 | Chang ................... 435/172.2 X |
| 4,681,848 | 7/1987 | Tsukamato ............. 935/104 X |

FOREIGN PATENT DOCUMENTS 122628 10/1984 European Pat. Off. .
168745  1/1986 European Pat. Off. .

OTHER PUBLICATIONS

Rubin, B. U. et al., (1983) *J. Immunol.* 130, 1019.
Hurrell, J. G. R., Monoclonal Hybridoma Antibodies: Techniques and Applications, pp. 16–19. CRC Press, Inc. 1982.
Bach, J. F., Immunology, p. 172, John Wiley & Sons, Inc. 1978.
Van der Meide et al., J. Immunol. Methods, 79:293–305(1985).
Le et al., J. Immunol. Methods, 69:61–70(1984).
Oleszak et al., Hybridoma, 2:439–449(1983).
Le et al., J. Immunol., 132:1300(1984).
Stefanos et al., J. Interferon Res., 5:39–43(1985).
Tanaka et al., J. Immunol. Methods, 77:275–282(1985).
Wang et al., Hybridoma, 3:321–332(1984).
Johnson et al., J. Immunol., 129:2357–2359(1982).
Berthold et al., Antiviral Res., Abstr 1:69(1984).
Novick et al., Antiviral Res., Abstr 1:75(1984).
Meager et al., Antiviral Res., Abstr 1:154(1984).
Miyata et al., Antiviral Res., Abstr 1:155(1984).
Stefanos et al., Antiviral Res., Abstr 1: 159(1984).

*Primary Examiner*—Christine M. Nucker
*Attorney, Agent, or Firm*—John H. C. Blasdale; James R. Nelson; Stephen I. Miller

[57] ABSTRACT

Monoclonal antibodies to γ-interferon and hybridomas producing such antibodies are disclosed. The antibodies are preferably of the immunoglobulin subclass IgG$_1$, κ, and do not bind to interferon-α$_2$.

4 Claims, No Drawings

MONOCLONAL ANTIBODIES TO GAMMA-INTERFERON, HYBRIDOMAS PRODUCING SUCH ANTIBODIES, AND KIT FOR USING SUCH ANTIBODIES

This is a continuation of application Ser. No. 26,722 filed as PCT EP86/00389 on Jul. 2, 1986 published as WO87/00182 on Jan. 15, 1987, now abandon.

SUMMARY

This invention relates to novel monoclonal antibodies γ-interferon hybridomas producing such antibodies, and to a kit for using such antibodies, e.g. in assaying or detecting γ-interferon.

BACKGROUND

It is well known in the art that it is possible to obtain a cell line which is able to produce a homogenous, i.e. monoclonal, antibody. The basic technique (Kohler and Milstein, Nature, 256, 1975) comprises the fusion of mouse myeloma cells with spleen cells to form hybridoma cells and selection from these of clones capable of producing the desired antibody. This general procedure has also been described in U.S. Pat. Nos. 4,364,932, 4,364,934, 4,364,935, 4,364,937 and 4,361,550.

Although the general method has been known for some years, the preparation and selection of each suitable hybridoma presents its own special difficulties. There is indeed no certainty that a suitable hybridoma will be found and, equally, there is no certainty that the hybridoma will produce an antibody having the desired properties.

Monoclonal antibodies have a variety of uses, in particular for the isolation and purification of the proteins to which they are specific or for assaying them e.g. in a diagnostic kit; see for example PCT published applications WO81/02899 and WO82/01773.

Whereas the family of human α-interferons is coded for by a number of distinct genes and thus shows variations in the amino acid sequences, human γ-interferon is coded for by only a single gene. However, human γ-interferon is a very labile protein and degrades in particular through shortening of its carboxy terminus to yield a number of smaller γ-interferons. Thus the complete amino acid sequence of human γ-interferon (GIF), as deduced from its cDNA sequence, is:

| S1 met | lys | tyr | thr | ser S20 | tyr 1 | ile | leu | ala | S10 phe | gln | leu | cys | ile | val 10 |
|---|---|---|---|---|---|---|---|---|---|---|---|---|---|---|
| leu | gly | ser | leu | gly | CYS | TYR | CYS | GLN | ASP 20 | PRO | TYR | VAL | LYS | GLU |
| ALA | GLU | ASN | LEU | LYS 30 | LYS | TYR | PHE | ASN | ALA | GLY | HIS | SER | ASP | VAL 40 |
| ALA | ASP | ASN | GLY | THR | LEU | PHE | LEU | GLY | ILE 50 | LEU | LYS | ASN | TRP | LYS |
| GLU | GLU | SER | ASP | ARG 60 | LYS | ILE | MET | GLN | SER | GLN | ILE | VAL | SER | PHE 70 |
| TYR | PHE | LYS | LEU | PHE | LYS | ASN | PHE | LYS | ASP 80 | ASP | GLN | SER | ILE | GLN |
| LYS | SER | VAL | GLU | THR 90 | ILE | LYS | GLU | ASP | MET | ASN | VAL | LYS | PHE | PHE 100 |
| ASN | SER | ASN | LYS | LYS | LYS | ARG | ASP | ASP | PHE 110 | GLU | LYS | LEU | THR | ASN |
| TYR | SER | VAL | THR | ASP 120 | LEU | ASN | VAL | GLN | ARG | LYS | ALA | ILE | HIS | GLU 130 |
| LEU | ILE | GLN | VAL | MET | ALA | GLU | LEU | SER | PRO 140 | ALA | ALA | LYS | THR | GLY |
| LYS 146 GLN. | ARG | LYS | ARG | SER | GLN | MET | LEU | PHE | ARG | GLY | ARG | ARG | ALA | SER |

The leader sequence consists of the 20 amino acid residues shown in small print and probably of the next three also. The various γ-interferons identified herein are given in the following Table:

| Interferon Type | Amino Acids |
|---|---|
| γ-interferon A or GIFA | 1–146 |
| γ-interferon A' or GIFA' | 1–142 |
| γ-interferon B or GIFB* | 1–131 |
| γ-interferon D or GIFD | 4–146 |

*GIFB is relatively inactive.

GIFA can be cleaved by CNBr at the methionine residues (amino acids 48, 80, 120 and 137). The resulting mixture of five cleavage products will be referred to as "CNBr-GIFA" herein.

In addition, a peptide consisting of the fifteen carboxy-terminal amino acids, 132–146, and identified herein as 15AA peptide, was used in the test procedures described herein.

The γ-interferons (GIFs) have in various tests proved to be most promising pharmaceutically active substances useful for combatting various diseases, in particular viral diseases and certain forms of cancer. γ-Interferon is widely described in the literature and may be obtained either by mitogenic induction of lymphocytes or by recombinant DNA technology, e.g. as described in the published European Patent Applications Nos. 77,760, 88,540 and 95,350.

DETAILED DESCRIPTION

It is clear that it is highly desirable to have antibodies which are specific to GIFs and which do not bind to α-interferons or to β-interferon and which indeed are capable of distinguishing between the various GIFs. The purpose of this invention therefore was to isolate monoclonal hybridomas which are able to produce monoclonal antibodies binding strongly to GIFs. As mentioned above, such antibodies are highly useful for various purposes, e.g. for assaying GIFs or for purifying GIFs (by affinity chromatography).

The present invention provides a number of monoclonal antibodies (Mabs) that recognize different epitopes on the GIF molecule and meet the following needs:

(a) Mabs that can be used to purify GIFs on an affinity chromatography column;
(b) Mabs that neutralize the biological activity of GIFs and can thus be used to test for GIFs;
(c) Mabs that can distinguish full-length GIFA from shorter (degraded) GIFs and in particular from less active GIFs (such as GIFB);
(d) Different Mabs that can be used as a pair in a sandwich ELISA (enzyme-linked immunosorbent assay).

The invention therefore provides monoclonal antibodies to γ-interferons (GIFs) produced by a hybridoma formed by fusion of cells from a mouse myeloma line and spleen cells from a mouse previously immunized with gamma interferon, which antibody does not bind to interferon $\alpha_2$, namely those designated 47-1, 3-6, 32, 35, 27, 22 and 9-11 herein.

The monoclonal antibodies of the present invention are preferably of the class $IgG_1$, κ, but may be of other classes, e.g. of $IgG_{2a}$, κ; they are produced from a hybridoma formed by fusion of NSI myeloma cells and spleen cells from a BALB/c mouse previously immunized with gamma interferon.

The hybridomas and the antibodies of this invention ray be obtained by the following procedure:

1. Mice are immunized with several injections of GIFA. The type of mouse used is not critical but good results are achieved with BALB/c females. The antigen may be applied in any suitable form, e.g. in complete Freund's Adjuvant (CFA) emulsified with phosphate buffered saline (PBS) (ratio 1:1). The number of injections and the quantity of antigen administered must be such that the number of antigen-specific splenocytes is sufficient. Usually, immunization consists of three intraperitoneal injections with 10 μg of antigen at about 2-week intervals. This is followed by a further boost consisting of 10 μg antigen in PBS intravenously and 10 μg antigen in CFA/PBS intraperitoneally.

2. The spleens of the immunized mice are removed and spleen cell suspensions are prepared. This procedure follows well-known techniques.

3. The spleen cells are fused with mouse myeloma cells. The technique for fusing myeloma cells with spleen cells is well known. Most preferably the fusion is achieved by warming a mixture of the two cell types with an appropriate fusion promoter, e.g. polyethyleneglycol (PEG) having an average molecular weight from about 1000 to about 4000 (PEG1000). Several mouse myeloma cell lines are known and easily available. Preferred are cell lines which are HGPRT-deficient (HGPRT=Hypoxanthine Guanosyl Phosphoribosyl Transferase) and accordingly will not survive in HAT (culture medium comprising hypoxanthine, aminopterine and thymidine). Preferably the myeloma cell line used should be of the non-secreting type in that it does not itself produce any antibody. A suitable cell line for the purpose of this invention is the so-called NSl cell line. These cells were derived from P3/X63-A8 myeloma cells by Kohler and Milstein.

4. The fused spleen cells are cultured in several separate containers (e.g. in 24-well plates) according to standard procedures. The cell cultures obtained in step 3 are mixtures of fused spleen cells (hybridoma cells), unfused spleen cells and unfused myeloma cells. Preferably the cultivation is carried out in a medium which will eliminate the unfused myeloma cell line, e.g. in a HAT medium. Those unfused spleen cells which are non-malignant will normally stop growing after a short period of time, whereas the fused cells, which are HGPRT+, can grow in HAT medium.

5. The supernatants of the hybridoma cells in each container are tested for the presence of anti-GIF antibodies. This test may conveniently be carried out by applying an enzyme-linked immunosorbent assay (ELISA). In the present case antibodies linked to the enzyme alkaline phosphatase were chosen, but other procedures can be used.

6. Hybridomas producing the desired antibodies are selected and then are cloned preferably by the limiting dilution technique.

7. The desired antibodies are produced by means of the selected hybridomas. This production may be achieved in vitro by culturing the hybridoma in a suitable medium followed by isolation of the antibody, but this method ray not yield sufficient quantities. For producing larger quantities of the antibody, an in vivo method is preferably used. The hybridoma is injected back into the peritoneal cavity of the mouse where it will cause production of ascites fluid containing substantial quantities of the desired antibody, which is then isolated according to standard procedures.

A number of hybridomas producing antibodies against GIFs are described herein, but it is considered that the present invention encompasses all monoclonal antibodies exhibiting the characteristics described herein.

Further included within the present invention are methods for preparing the monoclonal antibodies described above employing the hybridoma technique illustrated herein. A number of examples of hybridomas are given herein, but one skilled in the art could follow the immunization, fusion, and selection methods provided herein and obtain other hybridomas capable of producing antibodies having the reactivity characteristics described herein. Since the individual hybridoma produced from a known mouse myeloma cell line and spleen cells from a known species of mouse cannot be further identified except by reference to the antibody produced by the hybridoma, all hybridomas producing antibody having the reactivity characteristics described above are included within the subject invention, as are methods for making this antibody employing the hybridoma.

Further aspects of the invention are methods of treatment or diagnosis employing the monoclonal antibodies exhibiting the pattern of reactivity provided herein.

EXAMPLE

1. Immunization of Mice

BALB/c female mice were immunized by three injections at fifteen day intervals with 10 μg of recombinant (non-glycosylated) GIFA in CFA/PBS emulsion (1:1). A total volume of 0.2 ml was injected intraperitoneally into each mouse. Fifteen days after the third injection a boost was made by injecting 10 μg of antigen in CFA intraperitoneally and at the same time 10 μg of antigen in PBS intravenously. Four days after the last injection the mice were killed and each spleen was excised for fusion.

2. Cell Fusion

The spleen was suspended in PBS ($Ca^{++}$- and $Mg^{++}$-free) and a cell count was carried out (one spleen comprises approximately $10^8$ cells).

After filtration through sterile gauze, the cells were washed twice in cold $Ca^{++}$- and $Mg^{++}$-free PBS (GIBCO CAT 420). The mouse myeloma cells (NSl) were washed (3 times with the same type PBS) and the two cell types were mixed and centrifuged together. The mixture comprised about $10^8$ spleen cells and about $10^7$ NSl cells.

About 0.2 ml of supernatant was left over the cells. The pellet was disrupted by gentle agitation of the tube, and 1 ml of PEG 1000 (Merck Art. 9729), 50% in PBS without $Ca^{++}$ and $Mg^{++}$, was then added dropwise during 1 minute with constant agitation at 37° C. After thirty seconds of agitation at 37° C., the tube was filled slowly with warm PBS without $Ca^{++}$ and $Mg^{++}$ and centrifuged. The cells were then directly re-suspended in HAT medium and distributed into 24-well plates (1 ml per well with about $2 \times 10^6$ cells per well). At this stage, non-treated splenocytes (1:10 of each spleen) were added as feeder cells.

3. Culture of the Hybridoma Cells 24 hours after the fusion, 1 ml of HAT medium was added to each well. Fresh medium was added three times a week to all the wells. The selection was achieved by culturing the hybridomas in HAT medium during 3 weeks followed by culturing the cells during three subsequent weeks in HT medium (same medium but without aminopterine). Finally the cells are resuspended in normal culture medium (RPMI 1640 with 10% fetal calf serum (FCS)).

As soon as possible, the hybridoma cells were frozen using standard techniques. The supernatant was kept and tested for the presence of anti-GIFA antibodies.

4. Test (Screening) for Presence of Anti-GIFA Antibodies

A. Direct ELISA

The presence of anti-GIFA antibodies in the supernatants of the hybridoma cell cultures was tested by an enzyme-linked immunosorbant assay (ELISA). The use of antibodies linked to the enzyme alkaline phosphatase following classical techniques (see "Enzyme Linked Immunosorbant Assay"; A. Voller, D. Bidwell and A. Bartlett; Manual of Clinical Immunology, chapter 45, p. 359) was chosen and adapted for detection of monoclonal anti-GIFA antibodies. The test used comprised the following steps:

(1) Coat the plate with 150 nM GIFA per well (dilution 2.5 μg/ml in coating buffer; 0.2 ml per well) and maintain at 4° C. overnight; then shake out the liquid.

(2) Add 0.2 ml RPMI 1640 and 10% FCS per well and incubate 1 hour at room temperature; then wash four times with PBS-Tween.

(3) Add 0.2 ml of hybridoma supernatant per well and incubate 2 hours at room temperature; then wash four times with PBS-Tween.

(4) Add 0.2 ml alkaline-phosphatase-conjugated sheep anti-mouse Ig, diluted 1:500 in RPMI 1640 and 10% FCS and incubate 2 hours at room temperature; then wash four times with PBS-Tween.

(5) Add 0.2 ml PNPP in diethanolamine buffer and take readings after 15 minutes, 30 min., 45 min., and 1 hour.

The absorption of GIFA to the bottom of the plates (96 well plates; NUNC Immune plate I CAT No. 2-39454) was performed in coating buffer (carbonatebicarbonate buffer) containing 1.59 g $Na_2CO_3$, 2.93 g $NaHCO_3$, and 0.2 g $NaN_3$ per liter of distilled water. After one night at 4° C., the wells were saturated with protein by incubation for 1 hour at room temperature with culture medium containing RPMI 1640 and 10% FCS (0.2 ml per well).

The plate was then washed four times with PBS-Tween containing 8 g NaCl, 0.2 g $KH_2PO_4$, 2.9 g $Na_2HPO_4.12H_2O$, 0.2 g KCl and 0.5 ml Tween 20 in one liter distilled water (pH 7.4).

After incubation of the plate with hybridoma supernatants, the presence of mouse anti-GIFA antibodies was revealed by sheep anti-mouse immunoglobulins conjugated with alkaline phosphatase (e.g. NEI-500 from NEN).

After two hours' incubation with the conjugate and four subsequent washings, 0.2 ml of substrate solution was added. The substrate (paranitrophenyl phosphate; PNPP Sigma 104 phosphatase substrate ref.: 104–105) was dissolved (1 tablet of 5 mg for 5 ml of buffer) in a buffer containing 100 mg $MgCl_2.6H_2O$, 0.2 g $NaN_3$ and 97 ml diethanolamine in one liter distilled water (pH 9.8, adjusted with HCl). The optical density at 405 nm was read at different time intervals after addition of substrate (Autoreader MR580 from Dynatech). Strong positive hybridomas were selected for cloning.

B. Inhibition of Biological Activity of GIFA

The activity of GIFA on the enhancement of HLA Class I antigen-expression on cell line U937 was measured. The neutralizing activity of the hybridoma and clone supernatants was tested after incubation with GIFA.

The Bioassay/Enhancement of HLA Class I expression was tested as follows:

1. Culture conditions: U937 cells (a promonocytic cell line) were incubated for 3 days with GIFA (1 and 4 units/ml), some in the presence and some in the absence of MAb.
2. Quantitation of HLA expression: the cells were incubated with the W6/32 MAb directed against the HLA Class I antigen. Cells were then labelled with an FITC-conjugated antimouse Ig antibody (F(AB')2 fragments).
3. The intensity of expression of HLA Class I antigen was determined by flow cytometry.

C. Antiviral Assay

The protection of A549 cells from the cytopathic effect of the EMC (encephalomyocarditis) virus was used as a biological assay for human gamma IFN. The reaction is read using the MTT assay described T. Mossman et al. (Journal of Immunological Methods, 1983, 65, pp. 55–63). Live cells have the capability to reduce the tetrazolium salt MTT to a dark blue formazan. The intensity of the formazan can be quantitated with a spectrophotometer after dissolution of the crystals in isopropanol.

The assay is performed as follows:

1. 50 μl of a solution of GIFA in RPMI-10% FCS is distributed into wells of 96-well flat-bottom plates.
2. 100 μl of hybridoma supernatant (or a dilution of purified monoclonal antibodies) is added per well. Control wells are prepared where the antibodies are omitted.
3. After 1 hours' incubation at 37° C., $10^4$ freshly trypsinized A549 cells in 100 μl RPMI-10% FCS are added per well.
4. After 3 hours' incubation at 37° C., 50 μl of a solution containing EMC virus is added. The amount of EMC virus added is calibrated so as to obtain a complete lysis of the cells in 3 days.

5. After a 3 day incubation, the medium is removed and replaced with 100 μl fresh medium (RPMI-10% FCS).
6. 10 μl of MTT solution (3-(4,5-dimethylthiazol-2-yl)-2,5-diphenyl-tetrazolium bromide) at 5 mg/ml in PBS is added per well.
7. After 3 hours' incubation at 37° C., 150 μl of acidified isopropanol is added (3.2 ml 12.5N HCl per 1 liter isopropanol, Merck, Germany).
8. The formazan crystals are dissolved by thorough mixing. The optical density of the microwells is measured with a Dynatech MR580 autoreader using a test wavelength of 570 nm and a reference wavelength of 630 nm. The amount of formazan present in each well reflects the number of cells protected from the EMC virus by the interferon.

D. Immunoprecipitation of $^{125}$I-GIFA

GIFA, iodinated with $^{125}$I, was incubated with supernatants. A polyclonal anti-mouse Ig was added to precipitate the MAb. The precipitation was measured with a gamma-ray counter and the pellets were analysed on SDS-PAGE.

The immunoprecipitation assay was carried out as follows:
1. Labelling of interferon: GIFA was iodinated ($^{125}$I) with the Bolton-Hunter reagent (Amersham, England). Excess labelling reagent was separated from the iodinated interferon by Sephadex G25M chromatography.
2. Assay:
2A. $^{125}$I-GIFA was incubated with MAb for 30 minutes at 20° C.;
2B. The complex was precipitated with an antimouse antibody overnight at 4° C.;
2C. The pellet was washed twice with PBS and then transferred to another tube;
2D. Radioactivity was monitored in a γ-ray counter;
2E. The solubilized pellet was analyzed by SDS-PAGE and autoradiography.

5. Cloning

The hybridoma cells were cloned by the limiting dilution technique.

Hybrid cells were diluted in the culture medium and distributed into 96-well plates (flat bottom Linbro 76003-05) in order to have (0.2 ml per well). Peritoneal macrophages of BALB/c mice were used as feeder cells; these were collected by washing the peritoneal cavity of mice with HBSS (GIBCO Cat. No. 406) containing 1% antibiotics (penicillinstreptomycin) at 4° C. Usually the peritoneal macrophages recovered from one mouse were sufficient for one 96-well plate (about (2 to 4)×10$^5$ cells per well).

After about three weeks, the clones could be seen by eye. They were then transferred to 24-well plates. At this stage the clones were frozen as quickly as possible. The supernatants were then kept and tested for anti-GIFA activity.

A number of suitable clones were identified; their designations, their deposition numbers at the Institut Pasteur, Paris, France, and the designation of the MAbs (monoclonal antibodies) produced are given below:

| Clone Designation | Deposition No. | MAb |
|---|---|---|
| 30N47-1 | I-463 | 47-1 |
| 47N3-6 | I-466 | 3-6 |
| 47N30A32 | I-464 | 32 |
| 47N30A35 | I-465 | 35 |

| Clone Designation | Deposition No. | MAb |
|---|---|---|
| 47N38B27 | I-468 | 27 |
| 47N48B22 | I-469 | 22 |
| 47N9-11 | I-467 | 9-11 |

6. Production of Ascites Fluid

In order to obtain large amounts of monoclonal antibodies, ascites fluid was induced in BALB/c mice by injecting hybridoma cells.

Ten days before injection of the cells the mice were treated i.p. with 0.5 ml of pristane (2,6,10,14-tetramethyl-pentadecane, Aldrich T22802). After three washes of hybridoma cells with PBS Dulbecco (GIBCO 041.4040), the cell suspension was adjusted to 2.5×10$^7$ cells per ml and 0.2 ml injected into each mouse (5×10$^6$ cells per mouse). After a period of ten to twenty days, the ascites fluid could be collected. After a few days of rest it was possible to collect ascites fluid from each mouse again. At least two or three samples of ascites fluid were harvested from each mouse.

7. Isolation and Purification of the Monoclonal Antibodies From Ascites Fluids

Ammonium sulfate precipitation: 27 ml of ascites fluid was diluted four-fold in cold PBS and placed on ice. An equal volume of saturated (NH$_4$)$_2$SO$_4$ solution (4° C.) was added slowly with stirring over a period of several minutes: final (NH$_4$)$_2$SO$_4$ concentration was 50% saturation. The solution was left on ice for 30 min. and then centrifuged at 5000×g for 10–15 min. The pellet was recovered and dissolved in 15 ml of buffer containing 40 mM NaCl and 20 mM Tris-HCl, pH 7.8 (buffer A). The re-suspended pellet was dialyzed against 100 volumes of buffer containing 20 mM NaCl and 20 mM Tris-HCl, pH 7.8 (buffer B). Prior to ion exchange chromatography denatured protein was removed by centrifugation at 15,000×g for 10 min.

DEAE cellulose chromatography: DE 52 (Whatman), which had been equilibrated in buffer B, was packed into a column (2.5 cm×27 cm) giving a packed bed volume of 132 ml. Packing was carried out with a pumped flow rate of 45 ml/hr. Chromatography was performed at room temperature. Immediately prior to loading, the dialyzed sample was adjusted to the ionic conditions of buffer B. The sample was loaded at a flow rate of 50 ml/hr. After washing with buffer B (1/10 of bed volume) the column was eluted with a linear gradient of NaCl (40 mM–200 mM). The total gradient volume was 1 liter and the elution flow rate was 50 ml/hr; 10 ml fractions of eluate were collected.

8. Lyophilization

Eluate fractions were dialyzed against 1% (w/v) NH$_4$HCO$_3$ for 48 hrs. The final volume following dialysis was 168 ml. This pool was sterilized by filtration through a 0.22 Micron membrane filter (Falcon). 10 ml aliquots of filtrate were transferred into sterile bottles and lyophilized. Sterile conditions were maintained following lyophilization by using an automatic capping device.

CHARACTERIZATION AND SELECTION OF THE ANTI-GIFA ANTIBODIES

The characterization of a monoclonal antibody should provide the following information and the selection of a monoclonal antibody follows from this information used to provide criteria for selection:

(i) Determination of the specificity, i.e. to which type of γ-interferon will the antibody bind;
(ii) Determination of Ig subclass;
(iii) Determination of the effect the antibody has on biological functions of the molecule (in this case, of the γ-interferon).

1. Specificity of the monoclonal antibodies

The specificity was determined by using the ELISA test described under item 4A, the inhibition of Biological Activity described under items 4B and 4C, and the Immunoprecipitation Assay described under item 4D, all in the Example above.

2. Determination of Ig subclass

The isotype of the monoclonal antibodies purified from culture supernatants was tested by an indirect ELISA test. The plates were coated with 30 nM GIFA per well and treated with RPMI 1640 and 10% FCS as already described. The monoclonal antibodies diluted in RPMI 1640 and 10% FCS were allowed to fix to the antigen coated at the bottom for a period of 2 hours. The wells were then filled with a solution of antibodies directed against various mouse Ig subclasses (dilution 1:1000). All the anti-isotypes used here were produced in rabbits (IgM; IgG$_1$; IgG$_{2a}$; IgG$_{2b}$; IgG$_3$ and IGA; λ and κ). The presence of anti-isotype antibodies was detected by anti-(rabbit Ig) conjugated to alkaline phosphatase (AP). The conditions of incubation and the reading of the results were as described for the ELISA test above.

SCREENING AND RESULTS

I—SCREENING to Define Antibodies Recognizing Different Epitopes on GIFA

Hybrids and clones obtained upon fusion of spleen of GIFA-injected mice were screened in the four following assays:

(a) The direct ELISA was carried out as in item 4A: different GIFs (GIFA, GIFA', GIFB, GIFD, natural GIF, GIFA cleaved with CNBr (=CNBr-GIFA)), a peptide representing the 15 COOH-terminal amino acids (=15 AA peptide), and this peptide coupled to BSA (=BSA-peptide), were coated onto ELISA plates, at 30 nM/well.

(b) Neutralization Assay: This test was carried out as in items 4B and 4C of the Example, except that GIFA', GIFB, GIFD and a pure commercial preparation of γ-interferon (Interferon Sciences, New Brunswick, N.J., U.S.A.) were used in addition to GIFA.

(c) Immunoprecipitation Assay: various GIFs (GIFA, GIFA', GIFB, GIFD), and the 15 AA peptide [see Table 1 in "RESULTS" Section] were iodinated, incubated and assayed as described for GIFA under item 4D of the Example.

(d) Epitope study—Competition between MAbs for binding to GIFA (1) Using an ELISA Plates were coated with the rabbit antibody. 2 ng/ml GIFA were added. The Mab 22 conjugate was added in the presence of another monoclonal antibody. MAbs recognizing epitopes different from that recognized by Mab 22 should not inhibit the binding of the conjugate. MAbs equivalent to Mab 22 should inhibit the binding of the conjugate.

MAb 21 as well as the non-conjugated MAb 22 compete with the MAb 22 conjugate. MAbs 3-6, 32 and 9-11 do not compete with the conjugate. These can be used in a two-MAbs sandwich assay.

This test was carried out at follows:

1. A rabbit anti-GIFA polyclonal antibody was coated onto microtiter wells;
2. The incubation continued with GIFA for one hour;
3. Incubation continued with a mixture of a MAb to be assayed and MAb 22 coupled to AP (for one hour);
4. Incubation continued with the AP-substrate for one hour;
5. The optical density was read.

(2) Using the Immunoprecipitation Assay—Competition between GIFA and CNBr-GIFA for binding to MAb.

One of the approaches to localizing the epitope of the neutralizing antibodies on the GIFA molecule is to see if known fragments of a molecule inhibit precipitation of the whole molecule. As a test model this was first studied with MAb 3-6 which precipitates GIFA but not GIFB. The precipitation of GIFA could be inhibited by the 15 AA peptide and also by CNBr-GIFA. Then the CNBr-GIFA fragments were tested against MAbs 22 and 35 to see whether the precipitation of GIFA could be inhibited. The activity of MAb 22 was not inhibited whereas that of MAb 35 was. This test was carried out as follows:

1. CNBr-GIFA was mixed with $^{125}$I-GIFA and incubated with the MAb to be assayed;
2. The antibody was precipitated with a rabbit anti(-mouse (mouse Ig) antibody;
3. The radioactivity of the pellet was measured in the γ-ray counter.

II - RESULTS

DESCRIPTION OF THE ANTIBODIES

MAb 47-1, Class IgG$_{2a}$, κ:

In the direct ELISA it binds to GIFA, GIFA', GIFB, GIFD and CNBr-GIFA, but not to the BSA-peptide. It does not precipitate the different GIFs or their fragments. It does not neutralize the biological activity of any of the tested GIFs. It recognizes GIFs only when these are coated on to plastic or nitrocellulose sheets.

MAb 9-11, Class IgG$_1$, κ:

In the direct ELISA it binds to GIFA, GIFA', GIFB and GIFD, but not to the BSA-peptide and CNBr-GIFA. It does not precipitate GIFA, GIFA', GIFB, GIFD or the 15 AA peptide. It does not neutralize the biological activity of any of the tested GIFs. It may recognize the same epitope as MAb 47-1, but with a lower affinity.

MAb 3-6, Class IgG$_1$, κ:

In the direct ELISA it binds to GIFA, GIFD, the BSA-peptide and CNBr-GIFA but not to GIFA' and GIFB. It precipitates GIFA and GIFD and the 15 AA peptide but not GIFA' and GIFB. It does not neutralize the biological activity of the tested GIFs.

MAb 32, Class IgG$_1$, κ:

In the direct ELISA it binds to GIFA, GIFD and the BSA-peptide but not to GIFA', GIFB and CNBr-GIFA. It precipitates GIFA, GIFD and the 15 AA peptide but not GIFA' and GIFB. It does not neutralize the biological activity of the tested GIFs. It recognizes an epitope within the last 15 amino acids (132-146) of the GIFA molecule and is different from MAb 3-6.

MAb 35, Class IgG$_1$, κ:

In the direct ELISA it binds to GIFA, GIFA', GIFB, GIFD and the BSA-peptide, but not to CNBr-GIFA. It precipitates GIFA, GIFA', GIFB, GIFD and the 15 AA peptide. It neutralizes the biological activity of all the GIFs tested but preferentially that of GIFB. It differs from MAb 22 in that CNBr-GIFA can inhibit the precipitation of GIFA by MAb 35 but not by MAb 22 (Table 2).

MAb 27, Class IgG$_1$, κ:

In the direct ELISA it binds to GIFA, GIFA', GIFB and GIFD but not to BSA-peptide and CNBr-GIFA. It precipitates GIFA, GIFA', GIFB and GIFD but not the 15 AA peptide. It neutralizes the biological activity of all the tested GIFs.

MAb 22, Class IgG$_1$, κ:

In the direct ELISA it binds to GIFA, GIFA', GIFB and GIFD but not to the BSA-peptide and CNBr-GIFA. It precipitates GIFA, GIFA', GIFB and GIFD but not the 15 AA peptide. It neutralizes the biological activity of all the tested GIFs. When coupled to an insoluble matrix it is able to retain recombinant and natural GIFs which can then be eluted e.g. with acetic acid at pH 2.5.

As there is only a little competition between this antibody and MAb 27 in the assay (Table 3), these MAbs might recognize different epitopes.

DESCRIPTION OF KITS FOR GAMMA INTERFERON QUANTITATION

The invention further provides a kit based on at least one of the monoclonal antibodies described herein and in particular on two of them. These kits permit the quantitation of GIFs. A preferred kit will contain two different monoclonal antibodies (recognizing different epitopes on the GIFA molecule), a standard GIFA composition and preferably a reaction vessel for carrying out the test; this vessel for example can be a hemolysis tube (12×75 mm.) or a well in an appropriate plate, for example a 96-well plate. The first antibody can if desired be already coated to the inside of the reaction vessel but is preferably provided as a separate reagent. A standard GIFA solution (which can be diluted to various strengths for carrying out the test) will be necessary; it will normally be provided as a lyophilised composition from which a standard GIFA solution can be prepared, in particular a composition containing a stabilizer in a sealed vial and preferably stored under nitrogen or other inert gas. The second monoclonal antibody will have attached to it or as part of it a moiety capable of generating a detectable response, for example an enzyme capable of carrying out some test reaction, in particular a color reaction. This moiety can be alkaline phosphatase (AP), which can degrade paranitrophenylphosphate (PNPP) to paranitrophenol, which is detected by its yellow color. The readings can be carried out automatically; for example, tests run in a 96-well plate can be read in a Dynatech Autoreader which can be coupled to a computer to give an immediate printout of the readings. Alternatively, if the tests are carried out in the hemolysis tubes, the absorbances can be read in a spectrophotometer.

A more sensitive test can be carried out by coupling biotin to the second Mab and adding in a third step avidin conjugated to alkaline phosphatase. The avidin binds to the biotin and then the PNPP is added and the liberated paranitrophenol is read as before.

TABLE 1

CLASSIFICATION OF ANTIBODIES

| Clones | MAb and Ig Class | DIRECT ELISA | | | | | | IMMUNOPRECIPITATION | | | | | INHIBITION or NON INHIBITION (I or NI) OF BIOLOGICAL ACTIVITY | | | | |
|---|---|---|---|---|---|---|---|---|---|---|---|---|---|---|---|---|---|
| | | GIF A | GIF A' | GIF B | GIF D | BSA peptide (a) | CNBr peptide (b) | GIF A | GIF A' | GIF B | GIF D | pep (c) | GIFA | GIFA' | GIFB | GIFD | Nat IFN |
| 30N47-1 | 47-1 IgG$_{2a}$, κ | + | + | + | + | − | + | − | − | − | − | − | NI | NI | NI | NI | NI |
| 47N9-11 | 9-11 IgG$_1$, κ | + | + | + | + | − | + | − | − | − | − | − | NI | NI | NI | NI | NI |
| 47N3-6 | 3-6 IgG$_1$, κ | + | − | − | + | + | + | + | − | − | + | + | NI | NI | NI | NI | NI |
| 47N3OA32 | 32 IgG$_1$, κ | + | − | − | + | + | − | + | − | − | + | + | NI | NI | NI | NI | NI |
| 47N3OA35 | 35 IgG$_1$, κ | + | ± | ± | + | + | − | + | + | + | + | + | I | I | I | I | I |
| 47N48B22 | 22 IgG$_1$, κ | + | + | + | + | − | − | + | + | + | + | − | I | I | I | I | I |
| 47N38B27 | 27 IgG$_1$, κ | + | + | + | + | − | − | + | + | + | + | − | I | I | I | I | I |

(a): 15 AA C-terminal GIFA (C-peptide) coupled to BSA in ELISA
(b): GIFA cleaved by CNBr
(c): 15AA C-terminal of GIFA (C-peptide)

TABLE 2

RESULTS WITH THE COMPETITION ASSAY FOR BINDING OF GIFA AND CNBr-GIFA TO MAbs

| Combination of MAbs | Counts/Minute |
|---|---|
| 22 | 3017 |
| 22 + CNBr-GIFA | 3106 |
| 35 | 4368 |
| 35 + CNBr-GIFA | 412 |

TABLE 3

RESULTS WITH THE SANDWICH ELISA (COMPETITION ASSAY)

| Combination of MAb | Optical Density |
|---|---|
| 22 AP + medium | 0.939 |
| 22 AP + 22 | 0.423 |
| 22 AP + 27 | 0.744 |

In a preferred embodiment, two kits are provided, each kit containing two different monoclonal antibodies: one catcher; and one tracer provided as a biotin conjugate; and also a standard GIFA preparation, preferably lyophilised. The first kit detects only full-length GIFA molecules and uses MAb 3-6 as the catcher monoclonal antibody; the second detects all GIFs and uses MAb 35 as catcher; in each the trace is MAb 27, to which biotin is coupled.

Table I shows that MAb 3-6 does not bind to GIF molecules lacking the fifteen amino acids at the C-terminus. MAb 3-6 is therefore a suitable MAb for detecting and quantifying full-length GIF. The second kit has a sensitivity of 1.25 ng GIF/ml.

The first kit can be used for example to determine the concentration of full-length GIF, and the second kit to determine all GIF. The difference represents the GIF with amino acids deleted at the C-terminus.

The kits can also be used to measure GIF (recombinant or natural), in particular natural GIF in biological fluids e.g. in human sera. The kits can be used to monitor various pathological situations and in the follow-up of clinical trials.

We claim:

1. A method of determining the amount of gamma interferon having amino acids deleted at the C-terminus in a sample comprising the steps of:
   (a) determining the total amount of gamma interferon in said sample comprising the steps of:
      (i) adding the sample to a first monoclonal antibody acting as a catcher, said catcher being capable of recognizing gamma interferons of any length;
      (ii) incubating said first monoclonal antibody and said sample;
      (iii) adding a second monoclonal antibody acting as a tracer, said tracer being capable of recognizing gamma interferons of any length to a moiety capable of generating a detectable response;
      (iv) incubating; and
      (v) measuring said response to determine the total concentration of the gamma interferons of any length;
   (b) determining the amount of full length gamma interferon in said sample comprising the steps of:
      (i) adding the sample to a first monoclonal antibody acting as a catcher, said catcher being capable of recognizing essentially full length gamma interferons;
      (ii) incubating said first monoclonal antibody and said sample;
      (iii) adding a second monoclonal antibody acting as a tracer, said tracer being capable of recognizing gamma interferons of any length and said tracer being conjugated to a moiety capable of generating a detectable response;
      (iv) incubating; and
      (v) measuring said response to determine the concentration of the full length gamma interferon, and
   (c) calculating the difference in amounts round in steps (a) and (b).

2. The method of claim 1 wherein the catcher and tracer of step (a) are each independently selected from monoclonal antibodies 35, 27 and 22.

3. The method of claim 2 wherein the catcher of step (b) is selected from monoclonal antibodies 3-6 and 32.

4. The method of claim 3 wherein the tracer of step (b) is selected from monoclonal antibodies 35, 27 and 22.

* * * * *